United States Patent [19]

Zimmerman

[11] 4,273,124
[45] Jun. 16, 1981

[54] NASAL CANNULA

[76] Inventor: J. Earl Zimmerman, Rte. 3, Box 351, Pine Grove, Pa. 17963

[21] Appl. No.: 44,582

[22] Filed: Jun. 1, 1979

[51] Int. Cl.³ .............................................. A61M 3/00
[52] U.S. Cl. .................................... 128/245; 128/246
[58] Field of Search .................... 128/245, 246, 349 B, 128/240, 241, 250

[56] References Cited

U.S. PATENT DOCUMENTS

| 1,243,840 | 10/1917 | Jessup | 128/246 |
| 1,248,891 | 12/1917 | Nichols | 128/250 |
| 1,481,008 | 1/1924 | Hodlick | 128/250 |
| 2,434,875 | 1/1948 | Turnbull et al. | 128/250 |
| 3,903,893 | 9/1975 | Scheer | 128/246 |
| 4,029,095 | 6/1977 | Pena | 128/250 |

FOREIGN PATENT DOCUMENTS

| 321688 | 6/1920 | Fed. Rep. of Germany | 128/250 |
| 178630 | 4/1922 | United Kingdom | 128/250 |
| 532214 | 1/1941 | United Kingdom | 128/250 |

*Primary Examiner*—John D. Yasko
*Attorney, Agent, or Firm*—Burns, Doane, Swecker & Mathis

[57] ABSTRACT

A nasal cannula of the type to be connected to a fluid duct and positioned within the nose of a patient for administering therapeutic fluid. The cannula comprises a resilient bulbous member configured to fit snugly within and against the vestibule wall of one nasal cavity of the patient to form a tight seal with respect thereto while maintaining the other nasal cavity in communication with ambient surroundings. The bulbous member includes a passage therethrough for communicating the fluid duct with the nasal cavity so that fluid supplied through the duct is inhaled through the one nasal cavity and exhaled through the other nasal cavity and/or open mouth.

13 Claims, 12 Drawing Figures

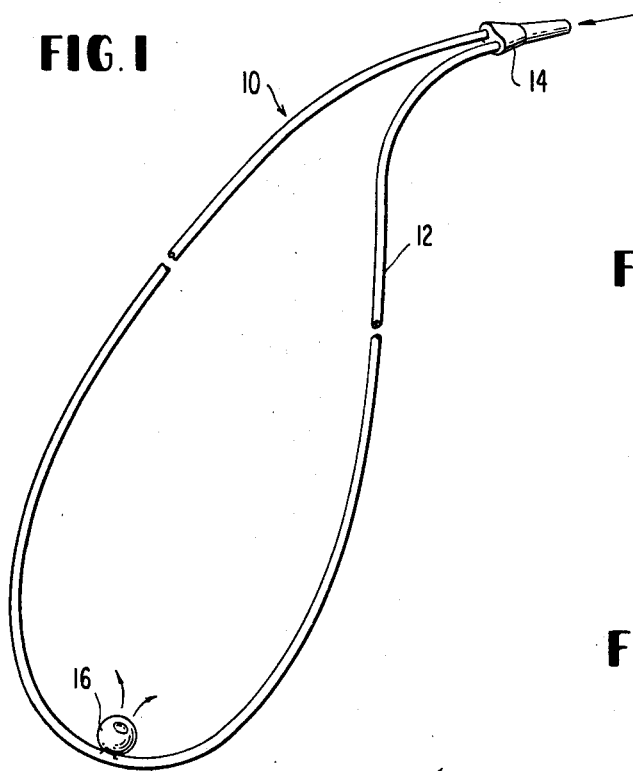
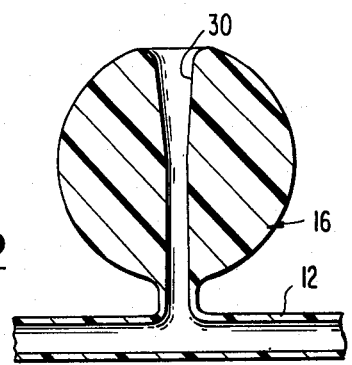
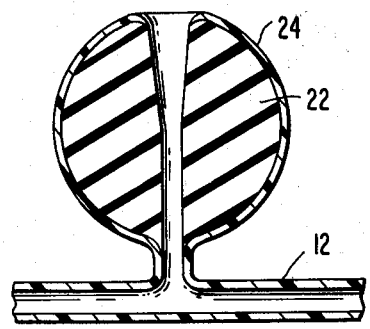
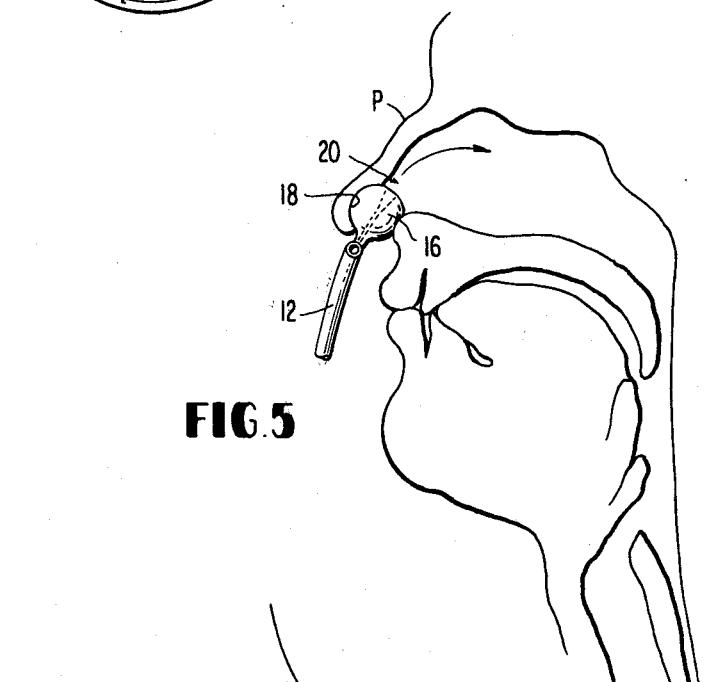
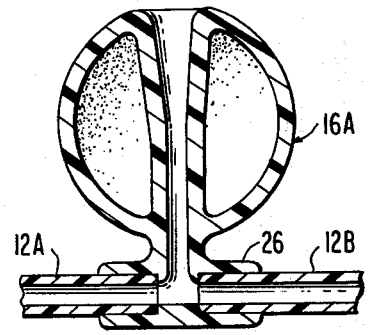
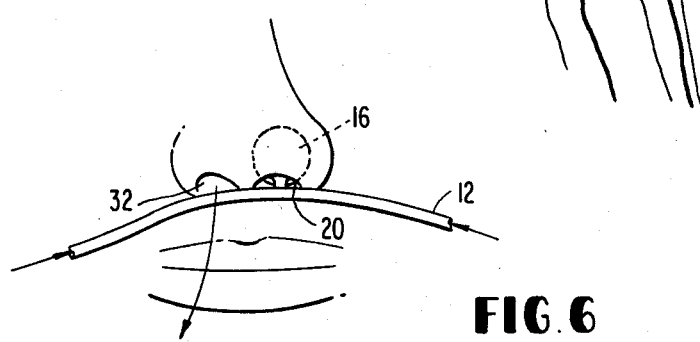

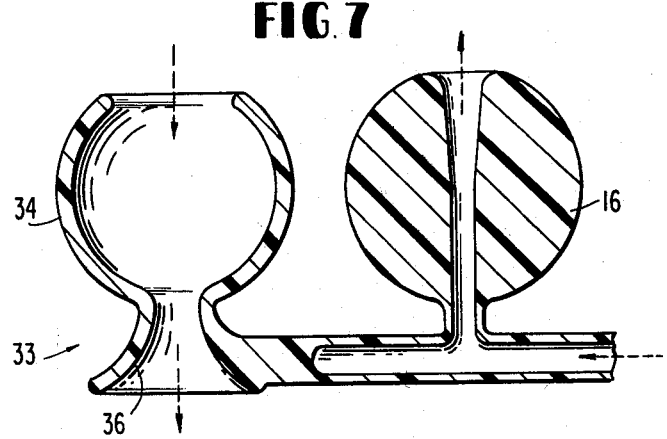
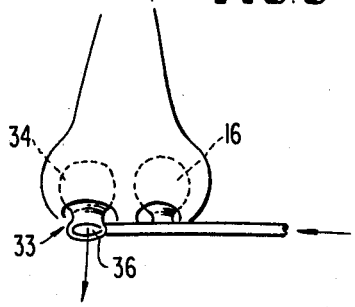
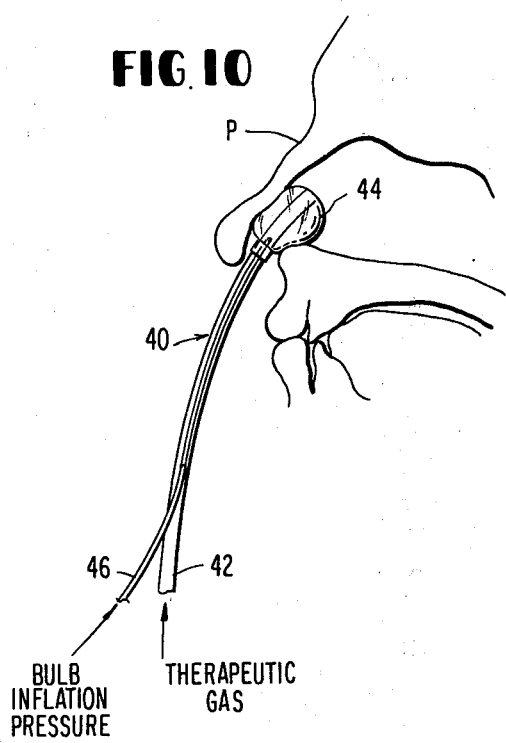
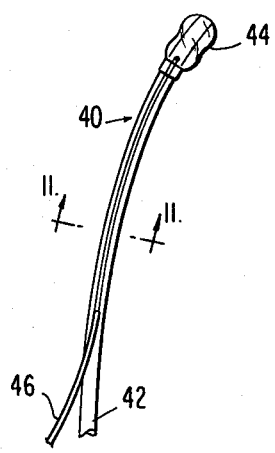
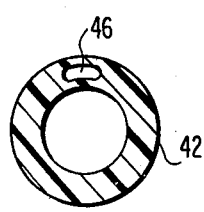
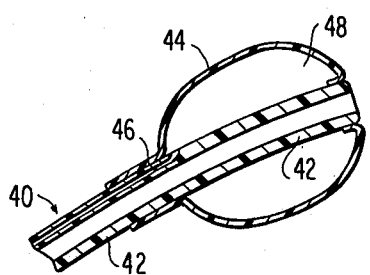

NASAL CANNULA

BACKGROUND AND OBJECTS OF THE INVENTION

The present invention relates to methods and apparatus for administering therapeutic gaseous substances into the nostril of a patient.

In the medical treatment of patients it is often necessary to delivery oxygen or other therapeutic gaseous substances to the patient's respiratory system. This has been heretofore achieved by means of nasal cannulas such as the type disclosed in U.S. Pat. No. 2,868,199 issued to Hudson on Jan. 13, 1959, and U.S. Pat. No. 3,726,275 issued to Jackson et al on Apr. 10, 1973.

In the medical treatment of patients it is also sometimes necessary to perform a surgical operation called tracheostomy or to perform endotracheal intubation, both of which involve significant risks. Among the purpose of these procedures is to eliminate a portion of dead space rebreathing of exhaled air containing carbon dioxide. There is presently no known way for reducing dead space ventilation other than endotracheal intubation or perform a tracheostomy.

Some nasal cannulas heretofore employed have comprised a flexible duct which is to be connected to a source of pressurized gas to be administered. A pair of short tubes communicate with the duct and are loosely received within the nasal cavities of the patient. When installed, the tubes are able to conduct gas from the duct to the nasal cavities, whereupon the gases are inhaled and exhaled by the patient.

The inhaled gases, which may comprise a mixture of room air and therapeutic gas, travel through each nasal cavity, and into the pharynx. The inhaled gases fill all voids and recesses within the nasal cavities before reaching the pharynx. Such voids may be considered "dead space" because the gases therein at the end of inhalation never reach the gas exchange areas of the lung, and are discharged during subsequent exhalation. It will be appreciated, then, that much of the inhaled gas will merely occupy the dead air spaces, rather than reach the gas exchange areas of the lung (i.e., the alveoli) to be of therapeutic benefit to the patient.

It can be understood that during exhalation, normally exhaled air with an increased carbon dioxide level (carbon dioxide produced in the body is a waste product of respiration) is exiting through the nasal and/or oral passages thus filling these cavities at the very end of exhalation. This spent respiratory air must necessarily be re-inhaled before and ahead of any therapeutic gas and/or ambient air.

Of course, the effects of dead air space can be reduced by tracheotomy or intubation which bypasses some of the dead space but such procedures involve significant risk and discomfort not present when using a cannula-type instrument, such as is an object of this invention. Conventional oxygen therapy cannulas do nothing to reduce the effects of dead space rebreathing. Breathing masks have also been employed, however, such masks actually increase effective dead air space, are relatively uncomfortable to the patient, and must be removed when eating, expectorating, etc., all of which demonstrates the need for new and improved methods and apparatus for administering therapeutic gases.

Thus, the only known effective ways of reducing the amount of dead space carbon dioxide the patient needs to re-inhale comprise hazardous tracheostomy or endotracheal intubation operations.

Another problem involved with the delivery of therapeutic gas via conventional nasal oxygen cannulas occur when the patient "mouthbreaths", i.e., has his mouth open during breathing. In such instances a substantial portion of the breathing action will be applied through the mouth rather than through the nose, thereby minimizing the amount of inhalation occurring through the nose. Accordingly, the therapeutic benefit of the gas thus administered will as least be greatly reduced. In such instances, reliance is placed on the chance that small amounts of unspent therapeutic gases will be exhaled from the nose to a location ahead of the mouth to be subsequently inhaled through the mouth.

Because a patient may readily change from nose breathing to mouth breathing and back again, the amount and concentration of therapeutic gas reaching his lungs varies greatly.

It is therefore, an object of the invention to minimize or obviate problems of the above-discussed type.

It is a further object of the invention to maximize the therapeutic benefit to a patient of nasal-supplied gases.

It is an additional object of the invention to provide methods and apparatus for administering the therapeutic gas through a patient's nose in a manner minimizing the effects of rebreathing of carbon dioxide laden dead space air within the nasal and/or oral cavities.

It is another object of the invention to minimize the amount of dead space carbon dioxide inhaled by a patient without the need for tracheostomy or endotracheal intubation.

It is an additional object of this invention to provide new, and more efficient and comfortable means of administering therapeutic gases in high concentration than with presently employed oxygen therapy masks.

SUMMARY OF THE INVENTION

These objects are achieved by the present invention which involves a nasal cannula of the type to be connected to a fluid duct and positioned within the nose of a patient for administering therapeutic fluid. The cannula comprises a resilient bulbous member configured to fit snugly within and against the vestibule wall of one nasal cavity of the patient to form a tight seal with respect thereto while maintaining the other nasal cavity in communication with ambient surroundings. The bulbous member includes a passage therethrough for communicating the fluid duct with the one nasal cavity so that fluid supplied through the duct is inhaled through the one nasal cavity and exhaled through the other nasal and/or oral cavities.

BRIEF DESCRIPTION OF THE DRAWING

Other objects and advantages of the invention will become apparent from the following detailed description of a preferred embodiment thereof in connection with the accompanying drawings in which like numerals designate like elements, and in which:

FIG. 1 is a perspective view of a cannula according to the present invention;

FIG. 2 is a longitudinal sectional view taken through a first type of bulbous portion of the cannula, FIG. 3 is a longitudinal sectional view taken through a second type of bulbous portion of the cannula;

FIG. 4 is a longitudinal sectional view taken through a third type of bulbous portion of the cannula;

FIG. 5 is an interior side view of a patient's head, depicting the bulbous portion of the cannula in snug fit with the wall of one nasal vestibule;

FIG. 6 is a front view of a patient's nose with the cannula installed therein;

FIG. 7 is a longitudinal sectional view through the bulbous portion of a second embodiment of a nasal cannula according to the present invention;

FIG. 8 is a front view depicting the cannula of FIG. 6 disposed in a patient's nose;

FIG. 9 is a side view of a third embodiment of a nasal cannula according to the present invention;

FIG. 10 is a side view through a patient's head depicting the manner in which the nasal cannula of FIG. 9 is installed;

FIG. 11 is a cross-sectional view taken along line 11—11 of FIG. 9; and

FIG. 12 is a longitudinal sectional view of the bulbous end of the cannula of FIG. 9.

DETAILED DESCRIPTION OF A PREFERRED EMBODIMENT OF THE INVENTION

A preferred nasal cannula 10 according to the invention is depicted in FIG. 1 and comprises a gas duct 12 formed of a suitable flexible material such as plastic. The ends of the duct 12 are mounted within a common fitting 14. Therapeutic gas is supplied continuously at a set flowrate through the fitting to both ends of the duct under a slight pressure which is conventional in treatments of this sort. The duct 12 is configured to encompass the neck of a patient.

Situated intermediate the ends of the duct is a bulbous member 16 from which the gas is to be administered to the patient P. The bulbous member is configured to fit snugly within the vestibule 18 of a nasal cavity 20, as depicted in FIG. 5. Preferably, the bulbous member 16 is of generally spherical configuration and is formed of a highly flexible material. For example, the bulbous member may be formed of a soft plastic material or, as depicted in FIG. 3, of a rubber or foam rubber center 22 with a plastic or rubber or other type of elastic skin 24 thereover (the skin serving to minimize friction during insertion into the nasal vestibule, to assure a fluid tight seal, or to provide for adjusting the size of the bulbous member).

The bulbous member may be formed integrally with the gas supply duct (FIG. 2), or it can be joined thereto as a separate component (FIG. 4). In the latter case, the bulbous member 16A may include a pair of tubular sleeves 26 which receive the ends of gas supply ducts 12A, B. The joining of the bulbous member and ducts 12A, B can be achieved in such manner that the bulbous member 16A is replaceable relative to the ducts.

Extending through the bulbous member is a central passage 30 (FIG. 2) which communicates at an inner end with the gas supply duct 12. Preferably, the passage 30 is of progressively larger cross-sectional area toward the outer end, to facilitate the travel of gas therethrough.

The bulbous member 16 can be installed within the nasal vestibule 18 by being manually compressed during insertion and then released for expansion within the vestibule. The bulbous member is sized slightly larger than the cross-sectional area of the nasal vestibule 18 so that the bulbous member tightly engages the inner walls of the vestibule 18. Due to the flexibility and elasticity of both the bulbous member 16 and the walls of the nasal vestibule 18, each is able to conform to the shape of the other and assure that a tight air seal is formed around the bulbous member during inhalation and exhalation by the patient.

IN OPERATION, the patient inhales through both nostrils 20, 32 (FIG. 6). Therapeutic gas only is being inhaled into the nostril with the bulbous member at a set flowrate while any additional gas to supply the patient's total inhalation flow rate must enter the other nostril open to ambient air. Since no appreciable air leakage occurs around the bulbous member, that portion of the breathing effort applied to the bulb-containing nasal cavity will receive only therapeutic gas from the bulb passage 30. (The total amount of therapeutic gas which is inhaled will be significantly greater than that normally inhaled from a conventional loose-fitting cannula due to the simultaneous inhalation of therapeutic gas which has filled and replaced dead space air in the other nasal cavity during the preceding exhalation.) The inhaled therapeutic gas from the dead air spaces within nasal passages enters the pharynx. During exhalation, all gas/air discharge occurs through the other, open nasal cavity 32 (exhalation through the bulb-containing nasal cavity is prevented by the air seal established by the bulbous member 16). During exhalation and during the slight pause following the very end of exhalation, therapeutic gas continues to flow into the nostril with the cannula and exits through the other nostril along with gas being exhaled from the lungs. In this way, expired air in the dead space is being washed out and replaced with therapeutic gas. The dead space now becomes a reservoir of therapeutic gas, rather than exhaled air, to be rebreathed. Thus, all unspent therapeutic gases occupying the dead air spaces in both nostrils at the end of exhalation remain, and are thereby positioned ahead of the subsequent inhalation of therapeutic gases and/or ambient air drawn-in during the ensuing inhalation. Accordingly, such unspent gases in the dead air spaces will be drawn-into the pharynx and will also mix with the charge of therapeutic gas from the cannula.

It will be appreciated that the air seal formed by the bulb 16 assures that all of the breathing effort which is applied to the bulb-containing nasal cavity 20 acts upon the incoming therapeutic gas (i.e., no ambient air is inhaled through that nostril which would dilute the therapeutic gas). This seal assures that the entire quantity of therapeutic gas administered will be delivered into the nasal cavity 20. This seal also assures that while therapeutic gas continues to flow during exhalation, it must enter and fill the other nostril from within before exiting through that nostril to the ambient surroundings. This means that the patient has no choice but to inhale these physiological reservoirs (dead spaces) of therapeutic gas ahead of and before any ambient air which may serve to dilute it. This method and apparatus makes it mandatory for the patient to breath the gas in the amounts being administered and thus affords a much more exacting control of what concentration the patient receives. Such quantity is appreciably greater than that normally inhaled into the nasal cavities from a conventional loose-fitting cannula. The significance of this fact will be appreciated when considering that the inhaled therapeutic gas from the bulbous member of the present invention is subject to mixing with exhaled gas in the dead air spaces of neither of the nasal cavities. The effects of the dead air spaces of the open nasal cavity 32 is, in effect, nullified since it is used as a physiological reservoir for therapeutic gas yielding an increase in the amount and therefore concentrations of therapeutic gas reaching the lung and essentially washing out and replacing carbon dioxide laden air with therapeutic gas containing no carbon dioxide.

In the case of mouth-breathing (discussed earlier) wherein a reduced amount of breathing takes place through the nose, therapeutic gas enters the pharynx and fills the oral cavities during exhalation similar to the way in which the open nostril functions so that all dead space cavities including the open mouth are essentially filled with therapeutic gas during exhalation and just before inhalation commences. This is an improvement over conventional loose-fitting cannula tubes in which little, if any, unspent therapeutic gas remains and fills the nasal and/or oral cavities following exhalation.

It will be appreciated that numerous modifications and embodiments are possible within the scope of the invention. For example, a cannula 33 comprising a pair of bulbous members 16, 34 can be provided for insertion into both nasal vestibules (FIGS. 7-8). A passage 36 through one of the bulbous members 34 communicates with ambient surroundings to enable the patient to exhale. By inserting two bulbous members into the nose, the intensity of attachment of the therapeutic device to the nose is increased.

Another embodiment of the invention is illustrated in FIGS. 9 and 12. A cannula 40 comprises a gas duct 42 to the end of which is mounted a closed membrane 44. The membrane is formed of a soft resilient material and forms a resilient bulbous component which can be inflated or deflated by means of a fluid passage 46, the latter communicating with the confined space 48 formed by the membrane. Pressurized gas or liquid is supplied to the passage 46 in any suitable fashion (e.g., from a syringe) to inflate the membrane before and/or after insertion into the nostril. The size of the bulbous component can be easily varied to suit the particular patient. The passage 46 can be valued to enable the bulbous component to be easily deflated. The walls of the duct 42 are made thick enough to prevent collapsing of same when the bulb is inflated. The bulb can be partially inflated before insertion and then fully inflated after insertion, so as to make insertion more comfortable while maximizing the intensity of the fluid seal.

Although the invention has been described in connection with a preferred embodiment thereof, it will be appreciated by those skilled in the art that additions, modifications, substitutions and deletions not specifically described may be made without departing from the spirit and scope of the invention as defined in the appended claims.

What is claimed is:

1. A breathing apparatus comprising a source of pressurized therapeutic gas, a nasal cannula directly connected to said gas source and positioned within the nose of a patient to administer the gas to the patient, said cannula comprising a resilient enlarged member configured to fit snugly against the vestibule wall of one nasal cavity of the patient to form a tight seal with respect thereto while maintaining the other nasal cavity in communication with ambient surroundings, said enlarged member including a passage therethrough for communicating the gas with the nasal cavity so that the gas supplied from said source is inhaled solely through said one nasal cavity and into the patient's lungs and exhaled solely through said other nasal cavity and/or open mouth of the patient.

2. Apparatus according to claim 1, wherein said enlarged member comprises a bulbous member of generally spherical configuration.

3. Apparatus according to claim 2, wherein said passage extends centrally through said bulbous member and terminates at an outer wall thereof.

4. Apparatus according to claim 1, wherein said cannula includes a second enlarged member to be positioned snugly within said other nasal vestibule and placed in communication with the ambient surroundings.

5. Apparatus according to claim 1, wherein said passage includes two inlets communicating with the gas source.

6. Apparatus according to claim 1, wherein said cannula includes a duct connected to said gas source, said enlarged member comprising means for being removably coupled to the duct.

7. An apparatus according to claim 1, wherein said bulbous member comprises an inflatable and deflatable element and means is provided for introducing and discharging fluid therefrom, said element being variable in size by varying the amount of fluid therewithin.

8. A nasal cannula for conducting therapeutic gas to one nasal cavity of a patient comprising:
a flexible gas duct for conducting therapeutic gas, and
a single resilient bulb mounted on said gas duct intermediate its ends,
said bulb being of generally spherical configuration to fit snugly within and against the wall of the nasal vestibule of said one nasal cavity to form an air seal during inhalation and exhalation by the patient,
said bulb including a passage extending therethrough and terminating at an outer wall thereof and communicating with said gas duct for conducting therapeutic gas to said one nasal cavity.

9. Apparatus according to claim 8, wherein said bulb comprises an inflatable and deflatable element, and means provided for delivering pressurized fluid to inflate said bulb.

10. A nasal cannula for conducting therapeutic gas to one nasal cavity of a patient comprising:
a flexible gas duct for conducting therapeutic gas, and
a single resilient bulb mounted on said gas duct intermediate its ends,
said bulb being engageable snugly within and against the wall of the nasal vestibule of said one nasal cavity to form an air seal during inhalation and exhalation by the patient,
said bulb including a passage extending therethrough and terminating at an outer wall thereof and communicating with said gas duct for conducting therapeutic gas to said one nasal cavity.

11. A method of administering therapeutic gas to a patient comprising the steps of providing a seal-forming member within one nasal vestibule of the patient in gas sealing relationship with the inner wall of such vestibule, communicating the other nasal vestibule with ambient surroundings and conducting the gas inwardly along a passage through the seal-forming member during an inhalation stroke of the patient, so that the gas is inhaled solely through said one nasal vestibule and into the patient's lungs and exhaled solely through the other nasal vestibule and/or open mouth of the patient.

12. A method according to claim 11, wherein said providing step comprises compressing a resilient bulbous member and inserting the compressed bulbous member into the nasal vestibule whereupon it expands to a larger size.

13. A method according to claim 1, wherein said providing step comprises inflating an inflatable-deflatable bulbous member by means of a separate fluid duct communicating with said bulbous member.

* * * * *